United States Patent
Chu et al.

(10) Patent No.: US 10,696,998 B2
(45) Date of Patent: Jun. 30, 2020

(54) REAGENTS AND METHODS FOR DETECTING ANALYTES

(71) Applicant: Ascensia Diabetes Care Holdings AG, Basel (CH)

(72) Inventors: Amy H. Chu, Elkhart, IN (US); Karen L. Marfurt, Edwardsburg, MI (US); Brenda L. Tudor, Elkhart, IN (US); Mary Ellen Warchal-Windham, Osceola, IN (US); Boru Zhu, Granger, IN (US)

(73) Assignee: ASCENSIA DIABETES CARE HOLDINGS AG, Basel (CH)

( * ) Notice: Subject to any disclaimer, the term of this patent is extended or adjusted under 35 U.S.C. 154(b) by 0 days.

(21) Appl. No.: 15/682,182

(22) Filed: Aug. 21, 2017

(65) Prior Publication Data

US 2017/0349929 A1  Dec. 7, 2017

Related U.S. Application Data

(63) Continuation of application No. 12/316,142, filed on Dec. 10, 2008, now abandoned.

(60) Provisional application No. 61/007,126, filed on Dec. 10, 2007.

(51) Int. Cl.
*G01N 27/26* (2006.01)
*C12Q 1/00* (2006.01)
*G01N 27/327* (2006.01)

(52) U.S. Cl.
CPC ............. *C12Q 1/004* (2013.01); *C12Q 1/005* (2013.01); *G01N 27/3271* (2013.01)

(58) Field of Classification Search
CPC .......................................... G01N 27/327–3278
See application file for complete search history.

(56) References Cited

U.S. PATENT DOCUMENTS

| | | | |
|---|---|---|---|
| 3,791,933 | A | 2/1974 | Wenz et al. |
| 3,791,988 | A | 2/1974 | Bauer et al. |
| 4,711,245 | A | 12/1987 | Higgins et al. |
| 4,746,607 | A | 5/1988 | Mura et al. |
| 5,108,564 | A | 4/1992 | Szuminsky et al. |
| 5,120,420 | A | 6/1992 | Nanki et al. |
| 5,128,015 | A | 7/1992 | Szuminsky et al. |

(Continued)

FOREIGN PATENT DOCUMENTS

| | | |
|---|---|---|
| EP | 0330517 | 2/1989 |
| EP | 0354441 | 2/1990 |

(Continued)

OTHER PUBLICATIONS

"Electrochemical Sensor for Measurement of Urea and Creatinine in Serum Based on ac Impedance Measurement of Enzyme-Catalyzed Polymer Transformation", Anal. Chem., W. Ho, S. Krause, C. McNeil, J. Pritchard, R. Armstrong, D. Athey, and K. Rawson, vol. 71, No. 10, May 15, 1999, pp. 1940-1946.

(Continued)

*Primary Examiner* — Bach T Dinh
(74) *Attorney, Agent, or Firm* — Nixon Peabody LLP

(57) ABSTRACT

A reagent for detecting an analyte comprises a flavoprotein enzyme, a mediator such as a phenothiazine mediator, at least one surfactant, a polymer and a buffer. The reagent may be used with an electrochemical test sensor that includes a plurality of electrodes.

8 Claims, 9 Drawing Sheets

(56) References Cited

U.S. PATENT DOCUMENTS

| | | |
|---|---|---|
| 5,206,147 A | 4/1993 | Hoenes |
| 5,262,035 A | 11/1993 | Gregg et al. |
| 5,264,104 A | 11/1993 | Gregg et al. |
| 5,288,387 A | 2/1994 | Pollmann et al. |
| 5,288,636 A | 2/1994 | Pollmann et al. |
| 5,320,725 A | 6/1994 | Gregg et al. |
| 5,356,786 A | 10/1994 | Heller et al. |
| 5,393,615 A | 2/1995 | Cory et al. |
| 5,437,999 A | 8/1995 | Diebold et al. |
| 5,498,542 A | 3/1996 | Cory et al. |
| 5,520,786 A | 5/1996 | Bloczynski et al. |
| 5,545,519 A | 8/1996 | Vadagama et al. |
| 5,582,697 A | 12/1996 | Ikeda et al. |
| 5,620,579 A | 4/1997 | Genshaw et al. |
| 5,628,890 A | 5/1997 | Carter et al. |
| 5,631,371 A | 5/1997 | Bloczynski |
| 5,631,863 A | 5/1997 | Fechner et al. |
| 5,653,863 A | 8/1997 | Genshaw et al. |
| 5,682,884 A | 11/1997 | Hill et al. |
| 5,695,947 A | 12/1997 | Guo et al. |
| 5,708,247 A | 1/1998 | McAleer et al. |
| 5,762,770 A | 6/1998 | Pritchard et al. |
| 5,798,031 A | 8/1998 | Charlton et al. |
| 5,820,551 A | 10/1998 | Hill et al. |
| 5,846,702 A | 12/1998 | Deng et al. |
| 5,854,074 A | 12/1998 | Charlton et al. |
| RE36,268 E | 8/1999 | Szuminsky et al. |
| 5,951,836 A | 9/1999 | McAleer et al. |
| 5,958,199 A | 9/1999 | Miyamto et al. |
| 5,997,817 A | 12/1999 | Crismore et al. |
| 6,153,069 A | 11/2000 | Pottgen et al. |
| 6,258,229 B1 | 7/2001 | Winarta et al. |
| 6,284,125 B1 | 9/2001 | Hodges et al. |
| 6,287,451 B1 | 9/2001 | Winarta et al. |
| 6,297,697 B2 | 10/2001 | Delano et al. |
| 6,413,398 B1 | 7/2002 | Geoff et al. |
| 6,413,411 B1 | 7/2002 | Pottgen et al. |
| 6,475,372 B1 | 11/2002 | Ohara et al. |
| 6,484,046 B1 | 11/2002 | Say et al. |
| 6,911,131 B2 | 6/2005 | Miyazaki et al. |
| 7,163,616 B2 | 1/2007 | Vreeke et al. |
| 2001/0006149 A1 | 6/2001 | Taniike et al. |
| 2002/0179442 A1* | 12/2002 | Miyazaki ............... C12Q 1/003 204/403.01 |
| 2003/0094384 A1* | 5/2003 | Vreeke ............... C12Q 1/32 205/777.5 |
| 2003/0146110 A1* | 8/2003 | Karinka ............... C12Q 1/002 205/777.5 |
| 2003/0159944 A1 | 8/2003 | Pottgen et al. |
| 2004/0208357 A1 | 10/2004 | Tokuhashi |
| 2005/0183953 A1* | 8/2005 | Su ............... G01N 27/3272 204/403.01 |
| 2007/0034512 A1 | 2/2007 | Yamaoka et al. |

FOREIGN PATENT DOCUMENTS

| | | |
|---|---|---|
| EP | 1074832 | 2/2001 |
| EP | 1293574 | 3/2003 |
| EP | 1691192 | 3/2004 |
| EP | 1486778 | 12/2004 |
| EP | 1707953 | 4/2006 |
| EP | 1742045 | 1/2007 |
| JP | H09509740 | 9/1997 |
| JP | 2003018619 | 1/2003 |
| JP | 2003185619 | 7/2003 |
| WO | WO198803270 | 5/1988 |
| WO | WO0173109 | 10/2001 |
| WO | WO03044511 | 5/2003 |
| WO | WO2006042304 | 4/2005 |
| WO | WO2005040407 | 5/2005 |
| WO | WO2006002432 | 1/2006 |
| WO | WO2006096619 | 9/2006 |

OTHER PUBLICATIONS

"Improvement of Screen-Printed Carbon Electrodes by Modification with Ferrocene Derivative", Sensors and Actuators, J. Razumiene, V. Gureviciene, A. Vilkanauskyte, L. Marcinkeviciene, I. Bachmatova, R. Meskys, and V. Laurinavicius, vol. 95, 2003, 378-383.

International Search Report—PCT/US08/086214 dated Mar. 3, 2009 (4 pages).

"Mediator Compounds for the Electrochemical Study of Biological Redox Systems: A Compilation", Analytica Chimica Acta, M. Fultz and R. Durst, vol. 140, 1982, 18 pages.

Oxford Dictionary of Biochemistry and Molecular Biology, 2000, 6 pages.

"Reduction of the interferences of biochemicals and hematocrit ratio on the determination of whole blood glucose using multiple screen-printed carbon electrode test strips", Analytical and Bioanalytical Chemistry, springer, Berlin, DE, vol. 389. No. 5. Oct. 3, 2007, 9 pages.

Written Opinion—PCT/US08/086214 dated Mar. 3, 2009 (7 pages).

Frias, J. et al., "Review of Adverse Events Associated with False Glucose Readings Measured by GDH-PQQ-Based Glucose Test Strips in the Presence of Interfering Sugars," Clinical Care/Education/Nutrition/Psychosocial Research, Diabetes Care, vol. 33, No. 4, Apr. 2010 pp. 728-729.

Igarashi, S. et al., "Engineering PQQ glucose dehydrogenase with improved substrate specificity, Site-directed mutagenesis studies on the active center of PQQ glucose dehydrogenase," Biomolecular Engineering 21 (2004) pp. 81-89.

Gorton, L., et al., "Electrocatalytic oxidation of NAD(P) H at mediator-modified electrodes," Reviews in Molecular Biotechnology 82 (2002) pp. 371-392.

* cited by examiner

FAD-GDH Source

| Sensor | %CV for 40% Hct Whole Blood | | | | | |
|---|---|---|---|---|---|---|
| | 36mg/dL | 66mg/dL | 110mg/dL | 220mg/dL | 330mg/dL | 627mg/dL |
| Low Salt Lot | 1.4 | 2.7 | 2.1 | 1.4 | 1.8 | 2.1 |
| High Salt Lot | 5.5 | 4.9 | 4.3 | 5.0 | 1.8 | 2.1 |

FIG. 11

REAGENTS AND METHODS FOR DETECTING ANALYTES

CROSS-REFERENCE TO RELATED APPLICATIONS

This application is a continuation of U.S. application Ser. No. 12/316,142, filed Dec. 10, 2008, now allowed, which claims priority to U.S. Provisional Application No. 61/007,126, filed Dec. 10, 2007, each of which is hereby incorporated by reference herein in its entirety the contents of which are incorporated entirely herein by reference.

FIELD OF THE INVENTION

The present invention relates generally to reagents, methods, and devices for measurement of analytes. More particularly, the present invention relates to reagents, methods, and devices for the measurement of glucose in a blood sample.

BACKGROUND OF THE INVENTION

The quantitative determination of analytes in body fluids is of great importance in the diagnoses and maintenance of certain physiological physical conditions. For example, lactate, cholesterol, and bilirubin should be monitored in certain individuals. In particular, it is important that individuals who have diabetes frequently check the glucose level in their body fluids to regulate the glucose intake in their diets. The results of such tests may be used to determine what, if any, insulin or other medication should be administered. In one type of blood-glucose testing system, test sensors are used to test a sample of blood.

A test sensor contains biosensing or reagent material that reacts with, for example, blood glucose. The testing end of the sensor is adapted to be placed into the fluid being tested (e.g., blood that has accumulated on a person's finger after the finger has been pricked). The fluid may be drawn into a capillary channel that extends in the sensor from the testing end to the reagent material by capillary action so that a sufficient amount of fluid to be tested is drawn into the sensor. The tests are typically performed using optical or electrochemical testing methods.

Electrochemical test sensors are based on enzyme-catalyzed chemical reactions involving the analyte of interest. In the case of glucose monitoring, the relevant chemical reaction is the oxidation of glucose to gluconolactone or its corresponding acid. This oxidation is catalyzed by a variety of enzymes; some of which may use coenzymes such as nicotinamide adenine dinucleotide (phosphate) (NAD(P)), while others may use coenzymes such as flavin adenine dinucleotide (FAD) or pyrroloquinolinequinone (PQQ).

In test sensor applications, the redox equivalents generated in the course of the oxidation of glucose are transported to the surface of an electrode, whereby an electrical signal is generated. The magnitude of the electrical signal is then correlated with glucose concentration. The transfer of redox equivalents from the site of chemical reaction in the enzyme to the surface of the electrode is accomplished using electron transfer mediators.

Electron transfer mediators previously used with FAD-glucose dehydrogenase (FAD-GDH) include potassium ferricyanide, phenazine-methosulfate (PMS), methoxy phenazine-methosulfate, phenazine methyl sulfate, and dichloroindophenol (DCIP). These compounds, however, have proven to be highly susceptible to the environmental conditions including temperature and moisture, which result in test sensor reagents of low stability. For example, during storage, reduced mediator may be produced from interactions between the oxidized mediator and the enzyme system. The larger the amount of mediator or enzyme, the larger the amount of reduced mediator that is produced. The background current, which increases over time, will generally increase toward the end of the shelf-life of the sensor strips because of the high concentration of reduced mediator. The increased background current may decrease the precision and accuracy of the measurements of the test sensor and, thus, provide a limited shelf-life for the test sensors.

Another disadvantage associated with existing test sensors is the relatively slow fill rate. Achieving a fast sensor fill rate is desirable so that the re-hydration of the reagent may be faster and more uniform. Thus, faster fill rates generally result in more precise, stable test sensors having less variation.

Therefore, it would be desirable to have a reagent that addresses one or more of these disadvantages.

SUMMARY OF THE INVENTION

According to one aspect of the present invention, a reagent for detecting an analyte comprises a flavoprotein enzyme, a mediator selected from the group

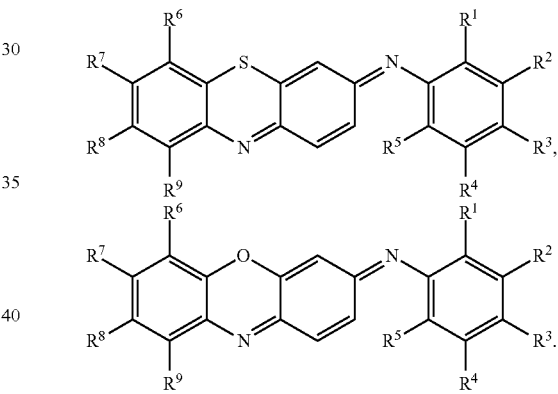

or a combination thereof. $R^1$, $R^2$, $R^3$, $R^4$, $R^5$, $R^6$, $R^7$, $R^8$, and $R^9$ are the same or different and are independently selected from the group consisting of hydrogen, alkyl, alkenyl, alkynyl, aryl, heteroaryl, cyclic, heterocyclic, halo, haloalkyl, carboxy, carboxyalkyl, alkoxycarbonyl, aryloxycarbonyl, aromatic keto, aliphatic keto, alkoxy, aryloxy, nitro, dialkylamino, aminoalkyl, sulfo, dihydroxyboron, and combinations thereof. The reagent further comprises at least one surfactant, a polymer and a buffer. At least one of the surfactant and the buffer includes an inorganic salt in which the ratio of the total inorganic salt to mediator is less than about 3:1.

According to another embodiment of the present invention, a reagent for detecting an analyte in a fluid sample includes FAD-glucose dehydrogenase having an activity of from about 0.1 Units/μA to about 10 Units/μL. The reagent further comprises a 3-(2',5'-disulfophenylimino)-3H-phenothiazine mediator having a concentration of from about 5 mM to about 120 mM. The reagent further comprises a surfactant having a concentration of from about 0.05 wt. % to about 0.5 wt. % of the reagent. The reagent further comprises a hydroxyethyl cellulose polymer having a concentration of from about 0.1 wt. % to about 4 wt. % of the reagent and a buffer. At least one of the surfactant and the buffer includes an inorganic salt in which the ratio of the total inorganic salt to mediator is less than about 3:1.

According to another embodiment of the present invention, an electrochemical test sensor comprises a working electrode having a surface. The test sensor further comprises a counter electrode having a surface. The test sensor further comprises a reagent coating at least a portion of the surface of the working electrode and at least a portion of the surface of the counter electrode. The reagent comprises a flavoprotein, a phenothiazine or a phenoxazine mediator, a buffer, and at least one surfactant and a polymer. At least one of the surfactant and the buffer includes an inorganic salt in which the ratio of the total inorganic salt to mediator is less than about 3:1.

According to one process of the present invention, a method of detecting an analyte in a fluid sample, the analyte undergoing a chemical reaction, comprises the act of providing an electrode surface. The method further comprises the act of facilitating flow of the fluid sample to the electrode surface using a surfactant. The method further comprises the act of catalyzing the chemical reaction with a flavoprotein enzyme. The method further comprising the act of generating a redox equivalent by the chemical reaction. The method further comprises the act of transferring the redox equivalent to the electrode surface using a phenothiazine or a phenoxazine mediator. The maximum kinetic performance is less than about 3 seconds.

According to another method, an analyte is detected in a fluid sample and includes providing an electrode surface. A reagent is provided that includes a flavoprotein enzyme and a mediator is selected from the group

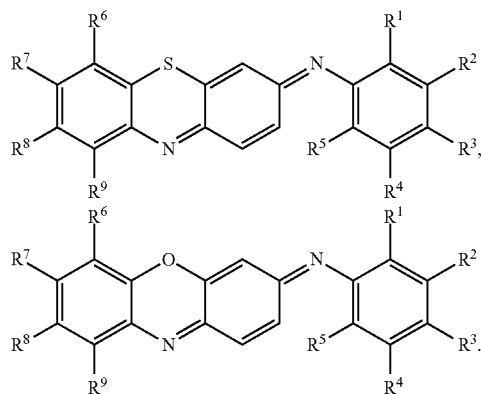

or a combination thereof, wherein $R^1$, $R^2$, $R^3$, $R^4$, $R^5$, $R^6$, $R^7$, $R^8$, and $R^9$ are the same or different, and are independently selected from the group consisting of hydrogen, alkyl, alkenyl, alkynyl, aryl, heteroaryl, cyclic, heterocyclic, halo, haloalkyl, carboxy, carboxyalkyl, alkoxycarbonyl, aryloxycarbonyl, aromatic keto, aliphatic keto, alkoxy, aryloxy, nitro, dialkylamino, aminoalkyl, sulfo, dihydroxyboron, and combinations thereof; at least one surfactant; and a buffer; the reagent contacting the electrode surface. The fluid sample contacts the reagent. The concentration of the analyte is determined. The maximum kinetic performance is less than about 3 seconds.

The above summary of the present invention is not intended to represent each embodiment, or every aspect, of the present invention. Additional features and benefits of the present invention are apparent from the detailed description and figures set forth below.

BRIEF DESCRIPTION OF THE DRAWINGS

FIG. 1b is a side view of the test sensor of FIG. 1a.
FIG. 11 is a graph with % CV for low salt reagent solutions and high salt reagent formulations.

Figure 1A:
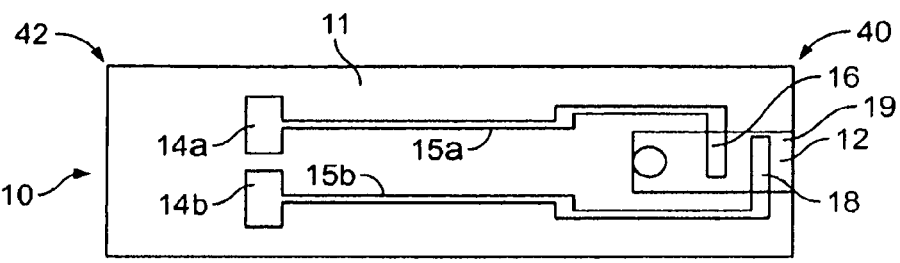
FIG. 1a is a test sensor according to one embodiment.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATED EMBODIMENTS

The present invention is directed to reagents, methods, and devices for measurement of analytes. More specifically, the present invention is directed to a test sensor reagent for detecting an analyte including (1) a flavoprotein enzyme, (2) a phenothiazine or phenoxazine mediator, (3) a buffer, (4) a surfactant or a combination of surfactants, and/or (5) a cellulose-based polymer.

The reagents described herein may be used to assist in determining an analyte concentration in a fluid sample. The nature of the analyte monitored in accord with the present invention is unrestricted, provided the analyte undergoes a chemical reaction that is catalyzed by a flavoprotein enzyme. Some examples of the types of analytes that may be collected and analyzed include glucose, lipid profiles (e.g., cholesterol, triglycerides, LDL, and HDL), microalbumin, hemoglobin, $A_{1C}$, fructose, lactate, or bilirubin. It is contemplated that other analyte concentrations may be determined. The analytes may be in, for example, a whole blood sample, a blood serum sample, a blood plasma sample, other body fluids such as ISF (interstitial fluid), urine, and non-body fluids.

The test sensors described herein are electrochemical test sensors. Meters used with the electrochemical test sensors may have optical aspects so as to detect the calibration information and electrochemical aspects to determine information related to the analyte (e.g., the analyte concentration) of the fluid sample. One non-limiting example of an electrochemical test sensor is shown in FIG. 1a. FIG. 1a depicts a test sensor 10 including a base 11, a capillary channel, and a plurality of electrodes 16 and 18. A region 12 shows an area that defines the capillary channel (e.g., after a lid is placed over the base 11). The plurality of electrodes includes a counter electrode 16 and a working electrode 18. The electrochemical test sensor may also contain at least three electrodes, such as a working electrode, a counter electrode, a trigger electrode, or another electrode to detect interference substances (e.g., hematocrit, ascorbate, uric acid) in the fluid sample. The working electrode employed in electrochemical sensors according to the embodiments of the present invention may vary, with suitable electrodes including, but not limited to, carbon, platinum, palladium, gold, combinations thereof, and the like.

The electrodes 16, 18 are coupled to a plurality of conductive leads 15a,b, which, in the illustrated embodiment, terminates with larger areas designated as test-sensor contacts 14a,b. The capillary channel is generally located in a fluid-receiving area 19. Examples of electrochemical test sensors, including their operation, may be found in, for example, U.S. Pat. No. 6,531,040 assigned to Bayer Corporation. It is contemplated that other electrochemical test sensors may be employed with the embodiments of the present invention.

The fluid-receiving area 19 includes at least one reagent for converting the analyte of interest (e.g., glucose) in the fluid sample (e.g., blood) into a chemical species that is electrochemically measurable, in terms of the electrical current it produces, by the components of the electrode pattern. The reagent typically includes an analyte-specific enzyme that reacts with the analyte and with an electron acceptor to produce an electrochemically measurable species that may be detected by the electrodes. The reagent may include mediators or other substances that assist in transferring electrons between the analyte and the conductor, binders that hold the enzyme and mediator together, other inert ingredients, or combinations thereof.

A fluid sample (e.g., blood) may be applied to the fluid-receiving area 19. The fluid sample reacts with the at least one reagent. After reacting with the reagent and in conjunction with the plurality of electrodes, the fluid sample produces electrical signals that assist in determining the analyte concentration. The conductive leads 15a,b carry the electrical signal back toward a second opposing end 42 of the test sensor 10 where the test-sensor contacts 14a,b transfer the electrical signals into the meter.

Figure 1B:
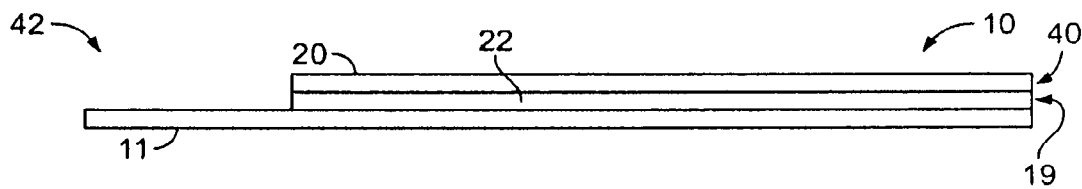

Referring to FIG. 1b, a side view of the test sensor 10 of FIG. 1a is shown. As shown in FIG. 1b, the test sensor 10 of FIG. 1b further includes a lid 20 and a spacer 22. The base 11, the lid 20, and the spacer 22 may be made from a variety of materials such as polymeric materials. Non-limiting examples of polymeric materials that may be used to form the base 11, the lid 20, and the spacer 22 include polycarbonate, polyethylene terephthalate (PET), polyethylene naphtalate (PEN), polyimide, and combinations thereof. It is contemplated that other materials may be used in forming the base 11, lid 20, and/or spacer 22.

To form the test sensor 10 of FIGS. 1a, 1b, the base 11, the spacer 22, and the lid 20 are attached by, for example, an adhesive or heat sealing. When the base 11, the lid 20, and the spacer 22 are attached, the fluid-receiving area 19 is formed. The fluid-receiving area 19 provides a flow path for introducing the fluid sample into the test sensor 10. The fluid-receiving area 19 is formed at a first end or testing end 40 of the test sensor 10. Test sensors of the embodiments of the present invention may be formed with a base and a lid in the absence of a spacer, where the fluid-receiving area is formed directly in the base and/or the lid.

Flavoproteins in accord with the present invention include any enzymes having flavin cofactors. Some non-limiting examples of flavoproteins include FAD-glucose oxidase (Enzyme Classification No. 1.1.3.4), Flavin-hexose oxidase (EC No. 1.1.3.5) and FAD-glucose dehydrogenase (EC No. 1.1.99.10). Additional oxidase enzymes for use in accord with the present invention include, but are not limited to, lactate oxidase, cholesterol oxidase, alcohol oxidase (e.g., methanol oxidase), d-aminoacid oxidase, choline oxidase, and FAD derivatives thereof. A desirable flavoprotein for use in accord with the present invention is FAD-glucose dehydrogenase (FAD-GDH).

Mediators in accord with the present invention include phenothiazines having the formula

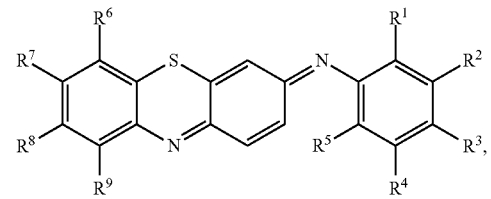

and phenoxazines having the formula

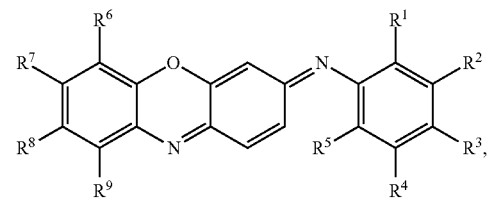

wherein $R^1$, $R^2$, $R^3$, $R^4$, $R^5$, $R^6$, $R^7$, and $R^9$ are the same or different and are independently selected from the group consisting of hydrogen, alkyl, alkenyl, alkynyl, aryl, heteroaryl, cyclic, heterocyclic, halo, haloalkyl, carboxy, carboxyalkyl, alkoxycarbonyl, aryloxycarbonyl, aromatic keto, aliphatic keto, alkoxy, aryloxy, nitro, dialkylamino, aminoalkyl, sulfo, dihydroxyboron, and combinations thereof. It is contemplated that isomers of the same may also be formed.

One desirable example of a phenothiazine that has been prepared and found to have suitable properties as an NADH mediator is a water-soluble sodium or ammonium salt of 3-(2', 5' disulfophenylimino)-3H-phenothiazine having the formula

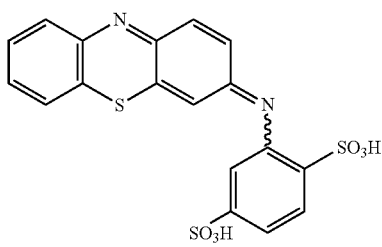 [SMILES: O=S(=O)(O)c1ccc(S(=O)(=O)O)c(N=c2ccc3nc4ccccc4sc-3c2)c1]

3-(2',5'-disulfophenylimino)-3H-phenothiazine is associated with a particularly low background current, which results in improved signal-to-noise ratios. Another desirable example is 3-(3', 5'-dicarboxy-phenylimino)-3H-phenothiazine mediator that has been prepared and found to have suitable properties as an NADH mediator. The background current of these phenothiazines was found to be significantly less than previously-used mediators.

Other phenothiazines and phenoxazines that have been found to have suitable properties as NADH mediators are 3-(4'-chloro-phenylimino)-3H-phenothiazine; 3-(4'-diethyl-amino-phenylimino)-3H-phenothiazine; 3-(4'-ethyl-phenylimino)-3H-phenothiazine; 3-(4'-trifluoromethyl-phenylimino)-3H-phenothiazine; 3-(4'-methoxycarbonyl-phenylimino)-3H-phenothiazine; 3-(4'-nitro-phenylimino)-3H-phenothiazine; 3-(4'-methoxy-phenylimino)-3H-phenothiazine; 7-acetyl-3-(4'-methoxycarbonylphenylimino)-3H-phenothiazine; 7-trifluoromethyl-3-(4'-methoxycarbonyl-phenylimino)-3H-phenothiazine; 3-(4'-ω-carboxy-n-butyl-phenylimino)-3H-phenothiazine; 3-(4'-aminomethyl-phenylimino)-3H-phenothiazine; 3-(4'-(2''-(5''-(p-aminophenyl)-1,3,4-oxadiazoyl)phenylimino)-3H-phenothiazine; 3-(4'-β-aminoethyl-phenylimino)-3H-phenothiazine; 6-(4'-ethylphenyl)amino-3-(4'-ethylphenylimino)-3H-phenothiazine; 6-(4'-[2-(2-ethanoloxy)ethoxy]-ethoxyphenyl)amino-3-(4'-[2-(2-ethanoloxy)ethoxy]ethoxyphenylimino)-3H-phenothiazine; 3-(4'-[2-(2-ethanoloxy)ethoxy]ethoxy-phenylimino)-3H-phenothiazine; 3-(4'-phenylimino)-3H-phenothiazineboronic acid, 3-(3',5'-dicarboxy-phenylimino)-3H-phenothiazine; 3-(4'-carboxyphenylimino)-3H-phenothiazine; 3-(3',5-dicarboxy-phenylimino)-3H-phenoxazine; 3-(2',5'-phenylimino)-3H-phenothiazinedisulfonic acid; and 3-(3'-phenylimino)-3H-phenothiazinesulfonic acid.

In one embodiment, a 3-(2', 5'-disulfophenylimino)-3H-phenothiazine mediator was prepared by dissolving phenothiazine (1.53 mole, 1.1 equivalent, 306 g) with stirring into 6.0 L of tetrahydrofuran (THF) and then cooled to 0° C. Aniline 2,5-disulfonic acid (1.38 mole, 350 g) was dissolved in 7.0 L of water and 1 M sodium hydroxide (NaOH) (128 ml) was added during stirring. The aniline 2,5-disulfonic acid solution was added slowly, over the course of about 2 hrs, to the phenothiazine solution, to give a white, cloudy suspension. The phenothiazine/aniline suspension was at a temperature of about 0° C. to about 4° C. Sodium persulfate (5.52 mole, 4 equivalent, 1314 g) was dissolved in 4.0 L of water to form a sodium persulfate solution.

The sodium persulfate solution was added dropwise over 3 hours to the phenothiazine/aniline suspension at a temperature between about 0° C. to about 3° C. and resulted in a very dark solution. The very dark solution remained cold using an ice bath and was stirred overnight. The contents were then transferred to a Buchi rotary evaporator and the tetrahydrofuran was removed over the course of about 2 hours at a temperature less than 35° C. After the evaporation act, the remaining solution was transferred to a 25 L separator and backwashed with ethyl acetate. The remaining solution was backwashed 3 times using 2 L of ethyl acetate each time. The reaction fluids were cooled while stirring to −3° C. in an acetone/$CO_2$ bath. The precipitated solid was filtered through two cloths on two 24 cm Buchner funnels on the same day. The precipitated solid was left overnight in the funnels to dry and then transferred to a flask containing 2 L of acetonitrile and stirred for about 1 hour at room temperature. To remove the residual water, the sample was then filtered and washed with more acetonitrile. The mediator was dried to a constant weight in a vacuum oven at 35° C.

Because of the low background current achieved using reagents having 3-(2',5'-disulfophenylimino)-3H-phenothiazine mediators, the same reagent formulation may be applied to both the working electrode and the counter electrode of an electrochemical test sensor. Applying the same reagent to both the working electrode and the counter electrode simplifies the manufacturing process and thereby decrease the costs associated therewith. Additionally, the low background current assists in obtaining accurate glucose readings, especially with samples having low glucose concentrations, which is particularly important in analyzing neonatal blood glucose assays.

The reagents of the embodiments of the present invention further include a surfactant or a combination of surfactants, and/or a cellulose-based polymer. The surfactant or combination of surfactants facilitates the sensor blood fill rate and re-hydration of a dry reagent. The faster blood fill rate and reagent re-hydration rate are desirable for achieving a quicker assay (e.g., less than 5-second assay) across an about 20% to an about 70% hematocrit range.

The surfactant is desirably selected from biocompatible ones including saccharide-based surfactants or phosphorylcholine-based surfactants. One non-limiting example of a saccharide-based surfactant is heptanoyl-N-methylglucamide (MEGA 8 from Sigma-Aldrich of St. Louis, Mo.). Surfactants such as MEGA 8 assist in increasing the thermal stability of test sensors. Additionally, surfactants such as MEGA 8 assist in fast fill rates, even for blood samples having high hematocrit levels. Using surfactants such as MEGA 8 with other inert ingredients (e.g., hydroxyethyl cellulose polymer and/or a neutral pH buffer) in a reagent formulation provides sensors with great stability, even at elevated temperatures. Non-limiting examples of phosphorylcholine-based surfactants include the Lipidure series (NOF Corporation, Japan).

Surfactants may also be selected from conventional neutral surfactants such as ethoxylated oleyl alcohol (Rhodasurf ON870 from Rhodia Inc. in Cranbury, N.J.). Surfactants may also be selected from anionic surfactants such as sodium methyl cocoyl taurate (Geropon TC-42 from Rhodia Inc.) and alkyl phenol ethoxylate phosphate (Phospholan CS131 from Akzo-Nobel Surface Chemistry LLC in Chicago, Ill.). It is contemplated that other surfactants may be used in forming the reagent.

Alternatively or additionally, the reagents of the embodiments of the present invention include a polymer. The reagents may include a cellulose-based polymer such as hydroxyethyl cellulose polymer. In some embodiments, the cellulose-based polymer is a low to medium molecular weight cellulose-based polymer. The polymer, such as a cellulose-based polymer, assists in providing the reagent with increased stability and adequate viscosity so that the reagent, when dried, stays in its original position on the sensor substrate. It is contemplated that other polymers may be used such as, for example, polyvinyl pyyrolidine (PVP).

The reagent may also include a buffer (e.g., a phosphate buffer) and/or other inert components. Non-limiting examples of suitable buffer solutions include but are not limited to Good's buffers (e.g., HEPES (i.e., N-2-hydroxyethylpiperazine-N'-2-ethanesulfonic acid), MOPS (i.e., 3-(N-morpholino)propanesulfonic acid), TES (i.e., N-tris (hydroxymethyl)methyl-2-aminoethanesulfonic acid)), McIlvaine's buffers, combinations thereof, or the like.

To provide a desirable assay precision, thermal stability and maximum kinetic performance, the ratio of the inorganic salts to mediator should be less than about 3:1. The source of inorganic salts could be from the buffer and/or the mediator. It is even more desirable for the ratio of the inorganic salts to mediator to be less than about 2:1 or even less than about 1.5:1.

According to one embodiment of the present invention, a reagent includes FAD-GDH, a low background phenothiazine mediator, a surfactant or combination of surfactants, a cellulose-based polymer, and a buffer to achieve improved sensor performance and stability. The reagent may be used to determine the glucose concentration in biological specimen such as blood, plasma, serum, or urine. In one embodiment, the phenothiazine mediator is 3-(2',5'-disulfophenylimino)-3H-phenothiazine. In another embodiment, the surfactant is MEGA 8 and the polymer is hydroxyethyl cellulose. In one embodiment, a reagent includes FAD-GDH having an activity ranging from about 0.1 Units/µL to about 10 Units/µL, about 5 mM to about 120 mM of 3-(2',5'-disulfophenylimino)-3H-phenothiazine mediator, about 0.05 wt. % to about 0.5 wt. % of MEGA 8 surfactant, about 0.1 wt. % to about 4 wt. % of hydroxyethyl cellulose, and about 25 mM to about 200 mM of buffer having a pH of about 4 to about 8. In another embodiment, a reagent includes FAD-GDH having an activity ranging from about 0.5 Units/µL to about 2.5 Units/µL, about 30 mM to about 60 mM of 3-(2',5'-disulfophenylimino)-3H-phenothiazine mediator, about 0.1 wt. % to about 0.4 wt. % of MEGA 8 surfactant, 0.01 to 0.1% of Geropon TC-42, about 0.2 wt. % to about 0.5 wt. % of hydroxyethyl cellulose, and about 50 mM to about 150 mM of buffer having a pH of about 6 to about 7.

Example 1

Figure 2:
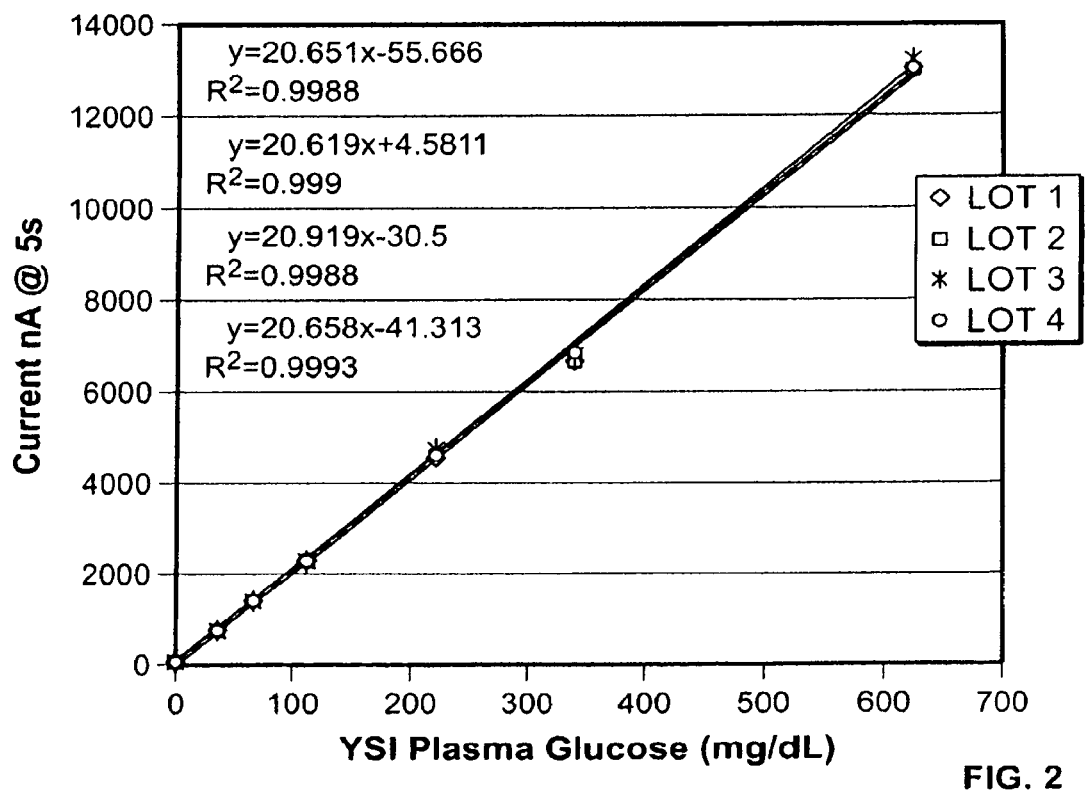
FIG. 2 is a line graph plotting current measurements against glucose concentrations.

As shown in FIG. 2, the reactivity of the chemistry for four sensor lots was analyzed by generating a glucose dose-response curve for sensors including FAD-GDH enzyme having an activity of about 1.75 Units/µL, about 40 mM 3-(2',5'-disulfophenylimino)-3H-phenothiazine mediator, about 0.2 wt. % MEGA 8 surfactant, about 0.25 wt. % hydroxyethyl cellulose, and about 100 mM phosphate buffer having a pH of about 6.5. The sensors were tested with whole blood samples at about 40% hematocrit level. The blood glucose concentrations of the blood samples were about 0 mg/dL, 38 mg/dL, 67 mg/dL, 112 mg/dL, 222 mg/dL, 339 mg/dL, and 622 mg/dL. For each blood sample, ten replicates were collected for each sensor lot. As shown in FIG. 2, the mean current for each sample was plotted against the sample glucose concentration (mg/dL) measured by a Yellow Springs Glucose Analyzer (YSI, Inc., Yellow Springs, Ohio) for each sensor lot. The slope of the dose response lines was about 20 nA/mg/dL, which indicates relatively high sensitivity of the test sensors. The y-intercepts were relatively close to 0 nA, which indicates low background noise levels. These results indicate that accurate readings may be achieved using the test sensors including the reagent described herein.

The coefficient of variation was determined for each of the ten replicates of the sensor lots used to generate the graph of FIG. 2. Table 1 below shows the average coefficient of variation percent (% CV) from the four sensor lots.

TABLE 1

| | Glucose Concentration | | | | | |
|---|---|---|---|---|---|---|
| | 38 mg/dL | 67 mg/dL | 112 mg/dL | 222 mg/dL | 339 mg/dL | 622 mg/dL |
| % CV | 3.1 | 2.1 | 3.4 | 2.5 | 2.1 | 1.2 |

Because of the low background noise of the sensors including the reagent of the embodiments of the present invention, the average assay % CV was less than 3.5%, even for samples having low glucose concentrations. Thus, the % CV values were well under 5%, which is often considered to be the standard acceptable limit. This low % CV indicates high precision of the test sensors. Additionally, the low % CV is associated with low variance among test sensors, which is desirable for obtaining consistent test results.

Example 2

Figure 3:
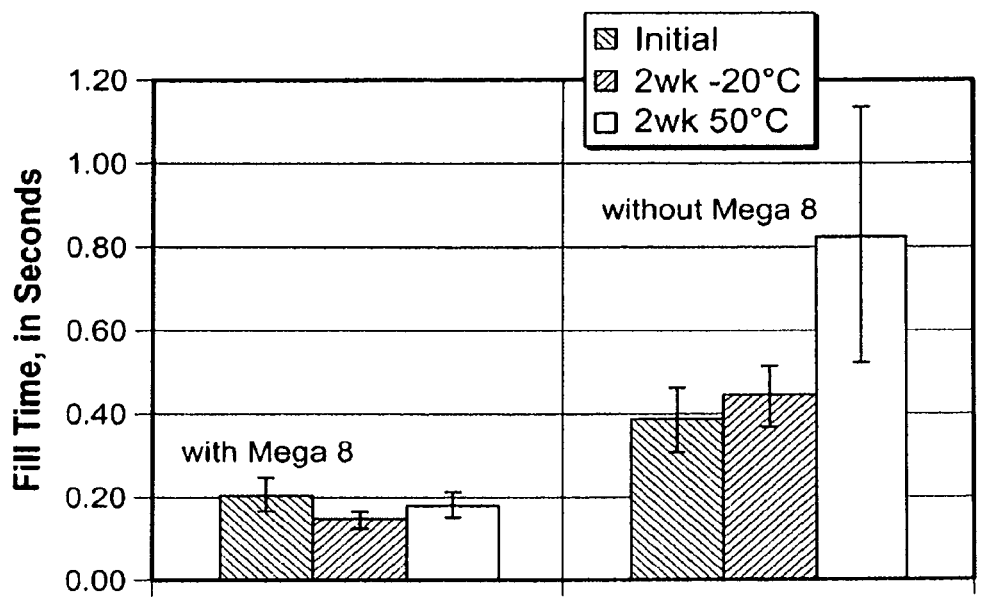
FIG. 3 is a bar graph comparing fill times of sensors including heptanoyl-N-methylglucamide (MEGA 8) surfactant with sensors not including MEGA 8 surfactant.

FIG. 3 shows a graph illustrating the affect of MEGA 8 surfactant on the sensor fill rate using 60% hematocrit whole blood. The test sensors used in FIG. 3 included FAD-GDH having an activity of about 1 Unit/µL (about 192 Units/mg), about 4 wt. % (about 120 mM) of potassium ferricyanide mediator, about 1.6 wt. % of the reagent of 4 wt. % hydroxyethyl cellulose, and about 35 mM of citrate buffer at a pH of about 5.0. Potassium ferricyanide mediator was used to test whether MEGA 8 surfactant without 3-(2',5'-disulfophenylimino)-3H-phenothiazine mediator had desirable affects on a test sensor. The fill rates of a group of thirty test sensors including about 0.2 wt. % MEGA 8 surfactant were compared against a control group of thirty test sensors not including MEGA 8 surfactant. Initial fill rates of ten sensors from each of the two groups of were measured. Ten sensors from each group were then exposed to a temperature of about −20° C. for about two weeks. Finally, ten sensors from each group were exposed to a temperature of about 50° C. for about two weeks. The average fill times of each group and subgroup of test sensors were calculated and are shown in FIG. 3. The blood fills the reaction chamber of the test sensor in less than 0.3 sec. with the reagent having surfactant and a 60% hematocrit whole blood sample. As shown in FIG. 3, the fill rate of the sensors including MEGA 8 surfactant was at least twice as fast and up to about four times faster than those sensors not including the MEGA 8 surfactant.

Example 3

Figure 4:
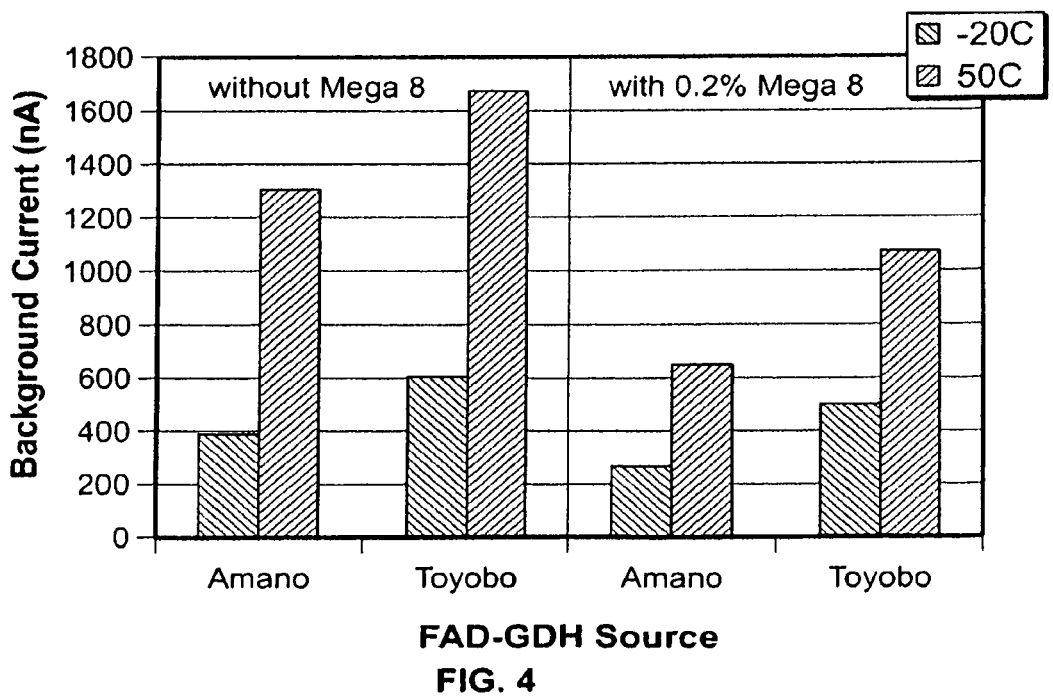
FIG. 4 is a bar graph comparing background current of sensors including MEGA 8 surfactant with sensors not including MEGA 8 surfactant.

The background currents of heat-stressed sensors including MEGA 8 surfactant were compared to the background currents of heat-stressed sensors not including MEGA 8 surfactant. The test sensors used in FIG. 4 included FAD-GDH having an activity of about 1 Unit/µL, about 50 mM of 3-(2',5'-disulfophenylimino)-3H-phenothiazine mediator, about 0.75 wt. % of the reagent of hydroxyethyl cellulose, and about 50 mM of buffer at a pH of about 7. A first group of forty test sensors did not include MEGA 8 surfactant. A second group of forty test sensors included about 0.2 wt. % MEGA 8 surfactant. Each of the first and second groups included two subgroups: a first subgroup including twenty test sensors having FAD-GDH from Amano Enzyme Inc. (Nagoya, Japan) and a second subgroup including twenty test sensors having FAD-GDH from Toyobo Co. (Osaka, Japan) Ten of the test sensors from each of the subgroups were stored at about 50° C. for about two weeks. The remaining test sensors were stored at about −20° C. for about two weeks. The background current of the sensors was then tested using 40% hematocrit whole blood samples having a glucose concentration of about 0 mg/dL. Ten replicates per sample were collected. FIG. 4 shows a graph illustrating the mean sensor background current from the ten replicates. As shown in FIG. 4, the test sensors including MEGA 8 surfactant had a significantly lower sensor background current change as compared with the test sensors not including MEGA 8 surfactant, indicating that the reagent is more stable when MEGA 8 surfactant is added to the reagent.

Example 4

The thermal stability of test sensors according to the embodiments of the present invention were also tested. The test sensors used in this example included FAD-GDH having an activity of about 2 Units/μL, about 40 mM of 3-(2',5'-disulfophenylimino)-3H-phenothiazine mediator, about 0.2 wt. % of MEGA 8 surfactant, about 0.25 wt. % of the reagent of hydroxyethyl cellulose, and about 100 mM of buffer at a pH of about 6.5. A first group of test sensors was stored at about 50° C. for about two weeks. A second group of test sensors was stored at about −20° C. for about two weeks. The performance of the sensors in each group was then evaluated with 40% hematocrit whole blood samples having glucose concentrations of about 50 mg/dL, about 100 mg/dL, and about 400 mg/dL. Ten replicates per sample were collected. The mean difference in glucose concentration between the test sensors stored at 50° C. and those stored at −20° C. was calculated and compared to several different types of self testing blood glucose monitoring systems. The glucose assay bias of the test sensors according to the embodiments of the present invention was negligible. Thus, there was no appreciable change in the glucose assay results even after storing the sensors at relatively extreme temperatures for two weeks. In contrast, the glucose assay bias of the comparative commercially available test sensors was generally from about 5% to about 12%. Thus, the thermal stability of the test sensors of the embodiments of the present invention was significantly better than that of existing test sensors.

Example 5

Figure 5:
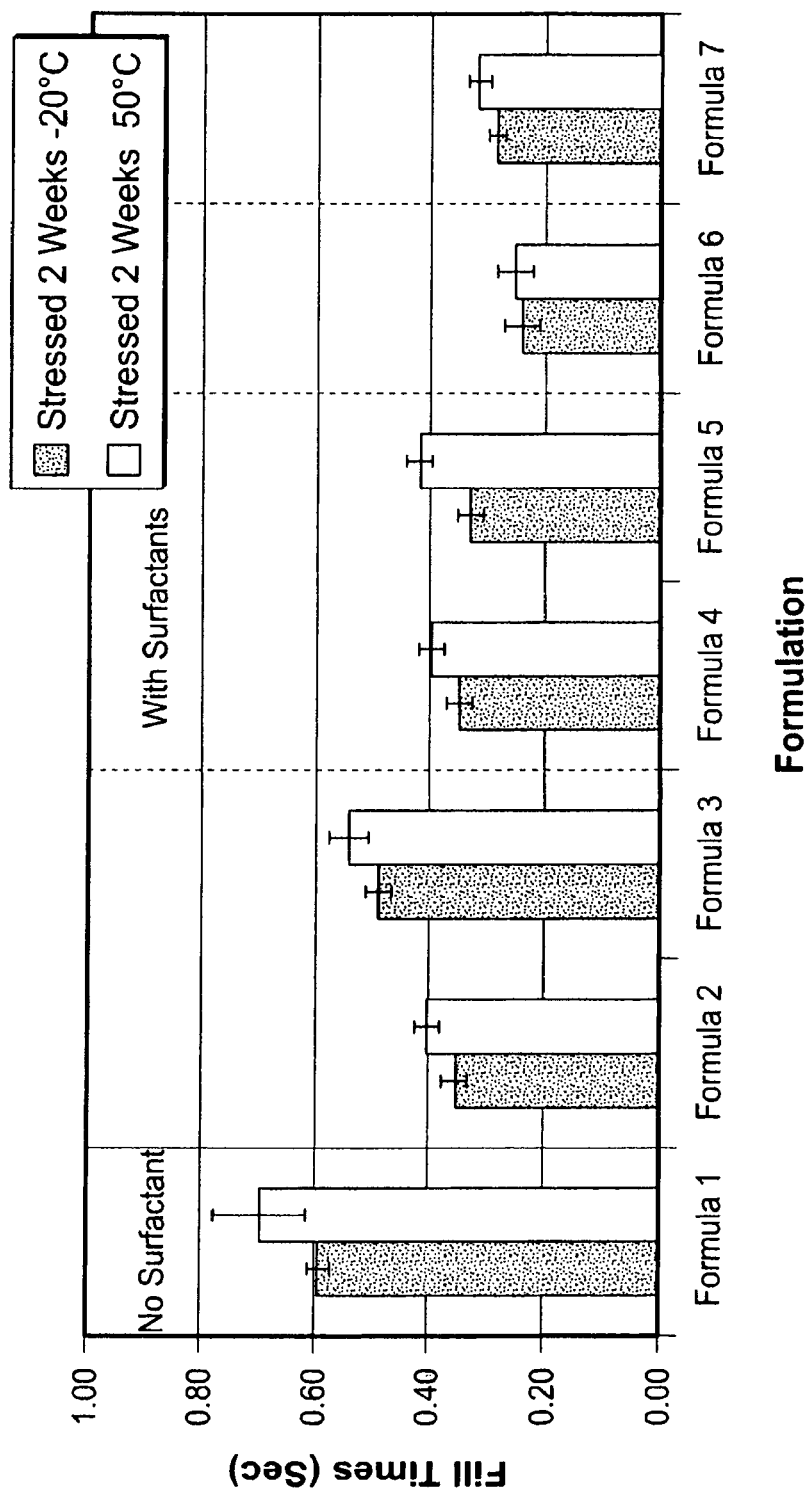
FIG. 5 is a bar graph of fill times of test sensors versus different formulations with and without surfactants.

Tests were performed using test sensors to determine fill speed with high hematocrit blood samples. Specifically, as shown in FIG. 5, a formulation using no surfactant (Formula 1) and surfactants (Formulas 2-7) were tested. The formulations are listed in Table 2 below.

Specifically, Formulas 2 and 3 included the surfactant MEGA 8, while Formulas 4 and 5 included the surfactant Rhodasurf. Formula 6 included the surfactant Zwittergent and Formula 7 included surfactants MEGA 8 and Phospholan CS131. Formulas 1-7 were stressed under two different conditions. Specifically, Formulas 1-7 were stressed for 2 weeks at a temperature of −20° C. and also stressed for 2 weeks at a temperature of 50° C.

After being stressed at these conditions, Formulas 1-7 were deposited onto electrodes on the test sensor. The sensors were tested in a vertical (90°) position with whole blood at 60-70% hematocrit. The sensors were videotaped during filling and the time was measured. The times required for the high hematocrit blood to fill the entire sensor reaction chamber for Formulas 1-7 are shown in FIG. 5. The sensor-fill time for Formula 1 (without surfactant) was about 0.6 and 0.7 sec. for the sensors stored at −20° C. and 50° C./2 wks., respectively. On the hand, Formulas 2-7 had sensor-fill times for both −20° C. and 50° C./2 wks. were about 0.5 sec. or less. Most of the Formulas 2-7 had sensor-fill times for both −20° C. and 50° C./2 wks. that were about 0.4 seconds or less with several being less than about 0.3 sec. Thus, Formulas 2-7 with surfactants had much improved fill times over Formula 1 without a surfactant.

Example 6

A reagent was tested to determine its maximum kinetic performance. The reagent included 40 mM of 3-(2',5'-disulfophenylimino)-3H-phenothiazine, 50 mM of phosphate buffer, 2.00 U/ul of FAD-GDH, 0.25 wt. % of hydroxyethyl cellulose (HEC) and 0.20 wt. % of the surfactant MEGA 8.

Figure 6:
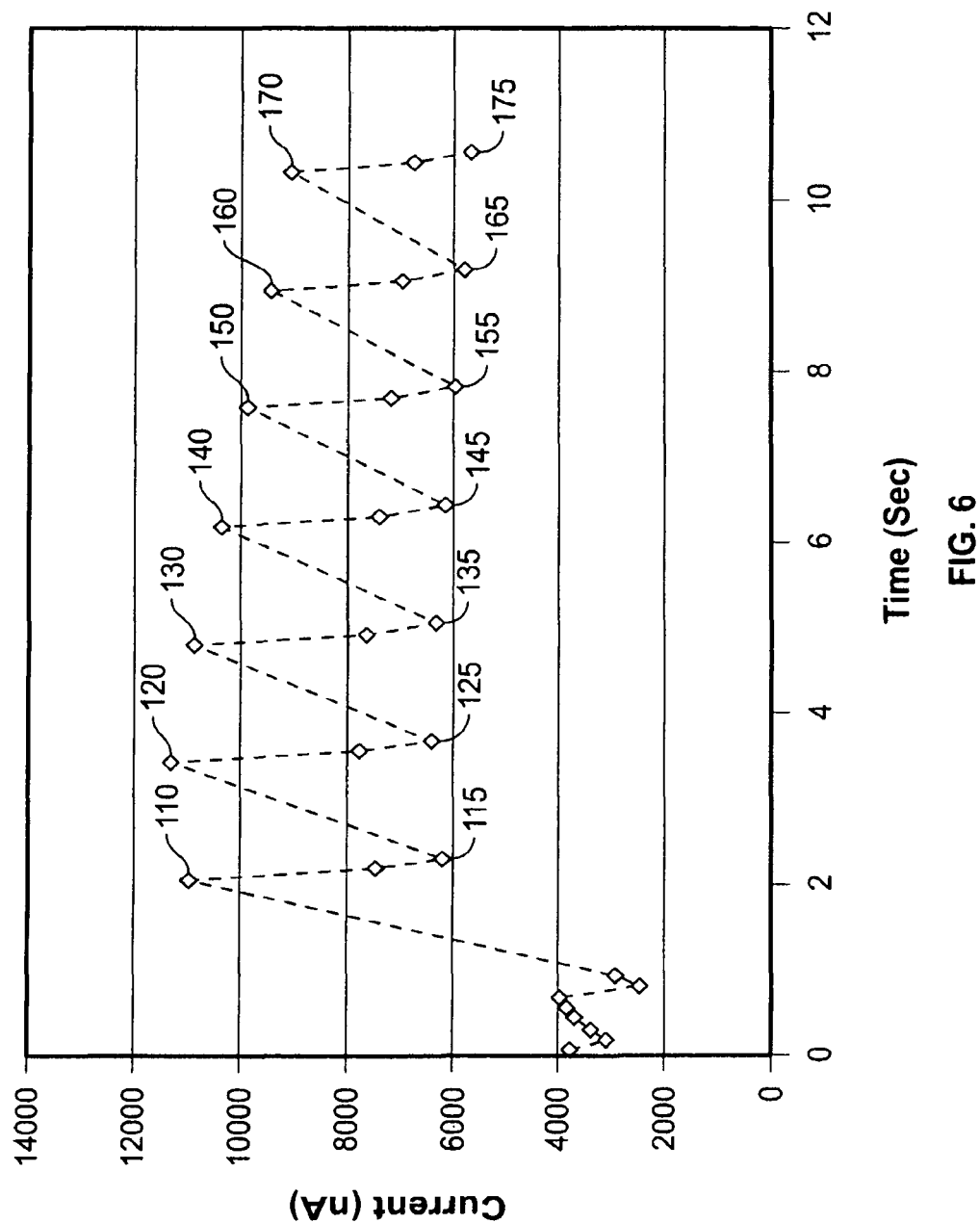
FIG. 6 is a plot of measured current values versus time in a formulation including a surfactant.

FIG. 6 shows the output signals from test sensors having blood samples with a glucose concentration of 400 mg/dL and 70% hematocrit. The signal input to the sensor strip by the measurement device was a gated amperometric pulse sequence that included eight pulsed excitations separated by seven relaxations, such as described in U.S. Patent Publication No. 2008/0173552. The excitations were less than a 1 second in duration. Three output current values were recorded during each excitation.

To correlate the output current values from the input signal with the analyte concentration of the sample, the initial current value from the excitation is preferably greater than those that follow in the decay. The output signals from the sensor strip of FIG. 6 showed an initial high current value that decays at about two seconds after the blood sample was introduced to the strip. Thus, the first output

TABLE 2

|  | Formula 1 | Formula 2 | Formula 3 | Formula 4 | Formula 5 | Formula 6 | Formula 7 |
| --- | --- | --- | --- | --- | --- | --- | --- |
| Mediator (mM) | 60 | 60 | 60 | 60 | 60 | 50 | 90 |
| Buffer (mM) | 75 | 75 | 75 | 75 | 75 | 100 | 112 |
| FAD-GDH (U/uL) | 3.00 | 3.00 | 3.00 | 3.00 | 3.00 | 1.25 | 3.75 |
| Polymer (HEC) (%) | 0.38 | 0.38 | 0.38 | 0.38 | 0.38 | 0.63 | 0.60 |
| MEGA 8 (wt. %) |  | 0.10 | 0.05 |  |  |  | 0.225 |
| Rhodasurf (wt. %) |  |  |  | 0.10 | 0.05 |  |  |
| Zwittergent 312 (wt. %) |  |  |  |  |  | 0.30 |  |
| Phospholan CS131 (wt. %) |  |  |  |  |  |  | 0.10 |

Mediator = 3-(2',5'-disulfophenylimino)-3H-phenothiazine
Buffer = Phosphate except Formula 6 used TES
TES = (N-tris(hydroxymethyl)methyl-2-aminoethanesulfonic acid)
HEC = hydroxyethyl cellulose currents having a high initial current value followed by decaying current values were observed in output current 110.

To correlate the output current values from the input signal to the analyte concentration of the sample, different sample analyte concentrations also preferably show a substantially constant difference between output signal current values. Preferably, the output current value or values correlated with the analyte concentration of the sample also are taken from a decay including current data reflecting the maximum kinetic performance of the sensor strip. The kinetics of the redox reaction underlying the output currents is affected by multiple factors. These factors may include the rate at which the reagent composition rehydrates, the rate at which the enzyme system reacts with the analyte, the rate at which the enzyme system transfers electrons to the mediator, and the rate at which the mediator transfers electrons to the electrode. Of these and other kinetic factors affecting the output currents, the rate at which the reagent composition rehydrates is believed to have the greatest influence on the output currents.

The maximum kinetic performance of the sensor strip may be reached during an excitation of a gated amperometric pulse sequence when the initial current value of an excitation having decaying current values is greatest for the multiple excitations. This may also be referred to as sensor-peak time. Preferably, the maximum kinetic performance of a sensor strip is reached when the last in time current value obtained for an excitation having decaying current values is the greatest last in time current value obtained for the multiple excitations. More preferably, the maximum kinetic performance of a sensor strip is reached when the initial current value of an excitation having decaying current values is greatest for the multiple excitations and the last in time current value obtained for the same excitation is the greatest last in time current value obtained for the multiple excitations.

The maximum kinetic performance of the sensor strip is desirably less than about 3 seconds and even more desirably less than about 2 seconds.

The gated amperometric pulse sequence used to determine the maximum kinetic performance of a test sensor included at least seven duty cycles, where the excitations are about 0.4 sec. in duration and the relaxations are 1 sec. in duration, include zero current flow through the sample, and are provided by an open circuit. At least three output current values are measured during each excitation. The potential input to the sensor strip is held substantially constant, at 250 mV and the sample temperature is at 23° C. Before the duty cycles, a pulse of 400 mV was applied for 0.9 seconds.

The sensor strip with 400 mg/dL of glucose in FIG. 6 reached maximum kinetic performance during the excitation decay that included output currents 120 and 125, between 3 and 4 seconds from the introduction of the sample to the sensor strip. This was established as both the greatest initial and the greatest last in time current values obtained from an excitation having decaying current values were present in the cycle that included output currents 120 and 125. Compare initial output current 120 with output currents 110, 130, 140, 150, 160 and 170 and also compare last in time output current 125 with output currents 115, 135, 145, 155, 165 and 175. Thus, the sensor reaches its maximum kinetic performance in between 3 and 4 seconds even for a 70% hematocrit blood sample Example 7

Figure 7:
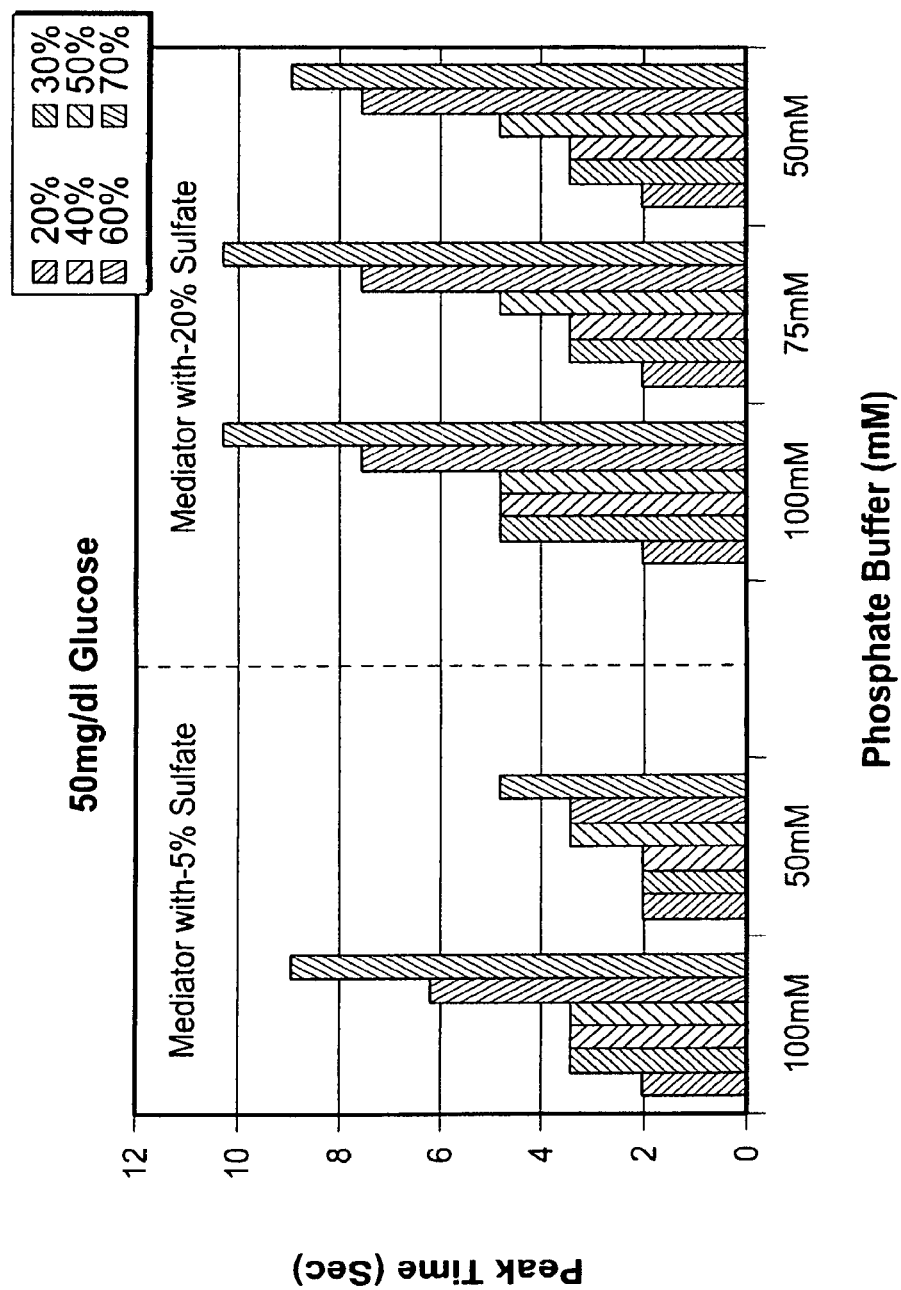
FIG. 7 is a bar graph of peak times using 50 mg/dL of glucose, mediators with different sulfate concentrations and different phosphate buffer concentrations.
Figure 8:
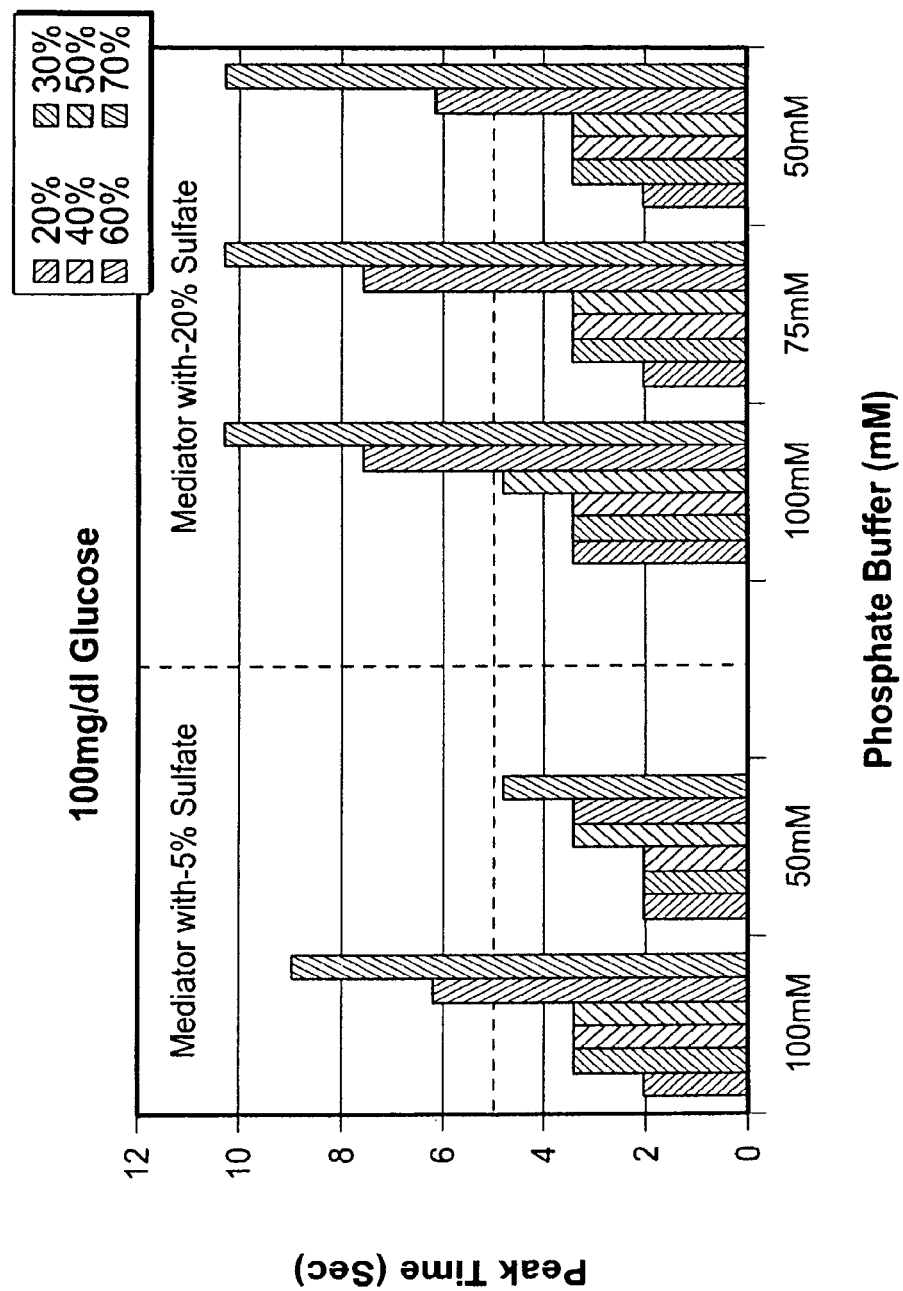
FIG. 8 is a bar graph of peak times using 100 mg/dL of glucose, mediators with different sulfate concentrations and different phosphate buffer concentrations.
Figure 9:
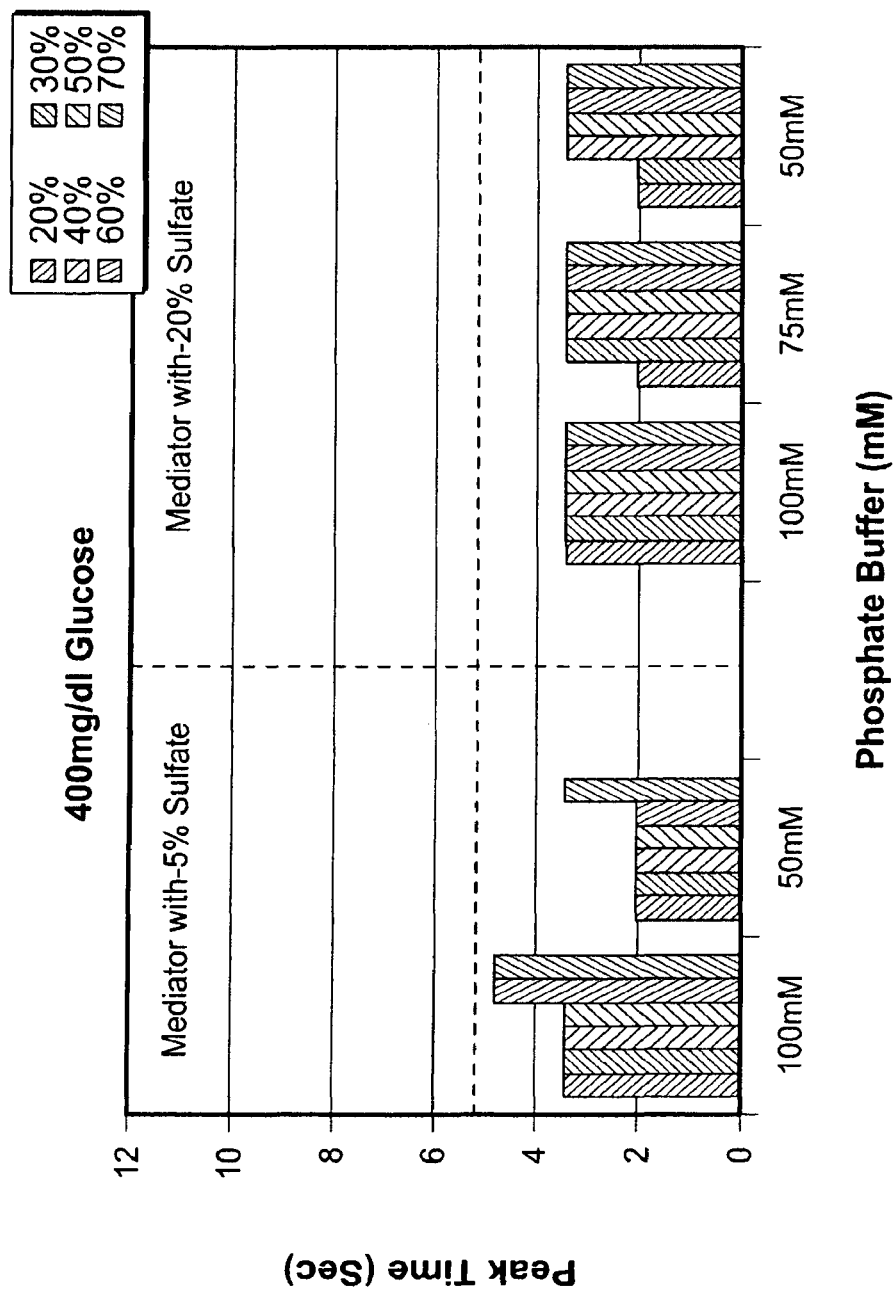
FIG. 9 is a bar graph of peak times using 400 mg/dL of glucose, mediators with different sulfate concentrations and different phosphate buffer concentrations.

FIGS. 7-9 show that the reagent formulation can also affect maximum kinetic performance for blood with different hematocrit levels. Referring initially to FIG. 7, at a glucose concentration of 50 mg/dL, the maximum kinetic performance using sensor-peak time increased as the hematocrit level increased. The mediator that included a smaller sulfate percentage (5% sulfate) generally had much faster peak times at comparable hematocrit levels and buffer concentrations. See, for example, at hematocrit level 60% using 50 mM phosphate buffer (compare 3.5 sec. with mediator using 5% sulfate and 7.5 sec. with mediator using 20% sulfate). The reagent formulation, such as buffer strength and residual sulfate content of the mediator, greatly impacts sensor reaction peak time, especially for samples with high hematocrit (>40%). Thus, high inorganic salt (from buffer or from the mediator in terms of sulfate concentration) in sensor formulation increases sensor-peak time (i.e., slows down sensor reaction). FIG. 8 shows similar results using 100 mg/dL of glucose concentration. Using the high glucose concentration of 400 mg/dL, FIG. 9 shows maximum kinetic performance using sensor-peak time generally below about 3 or 3.5 seconds with a number of sensor-peak times of 2 seconds. The mediator with 5% sulfate and 100 mM of phosphate buffer at high hematocrit levels had a maximum kinetic performance using sensor-peak time of about 4.5 or 5 seconds.

Thus, as shown in the 50 mg/dL and 100 mg/dL glucose concentrations, to achieve a fast reagent re-hydration and glucose reaction for samples with high hematocrit, the salt content in reagent formulations has to be lowered.

Example 8

Two formulations were tested for Maximum kinetic performance after the test sensors had been stored under stressed conditions (−20° C. and 50° C./4 wks.). The formulation in FIG. 10a included 50 mM phosphate buffer and a 3-(2',5'-disulfophenylimino)-3H-phenothiazine having 5 wt. % sulfate. The formulation in FIG. 10b included 100 mM phosphate buffer and a 3-(2',5'-disulfophenylimino)-3H-phenothiazine having 20 wt. % sulfate. The gated amperometric pulse sequence used in this Example was similar to that described in Example 6 above.

Figure 10A:
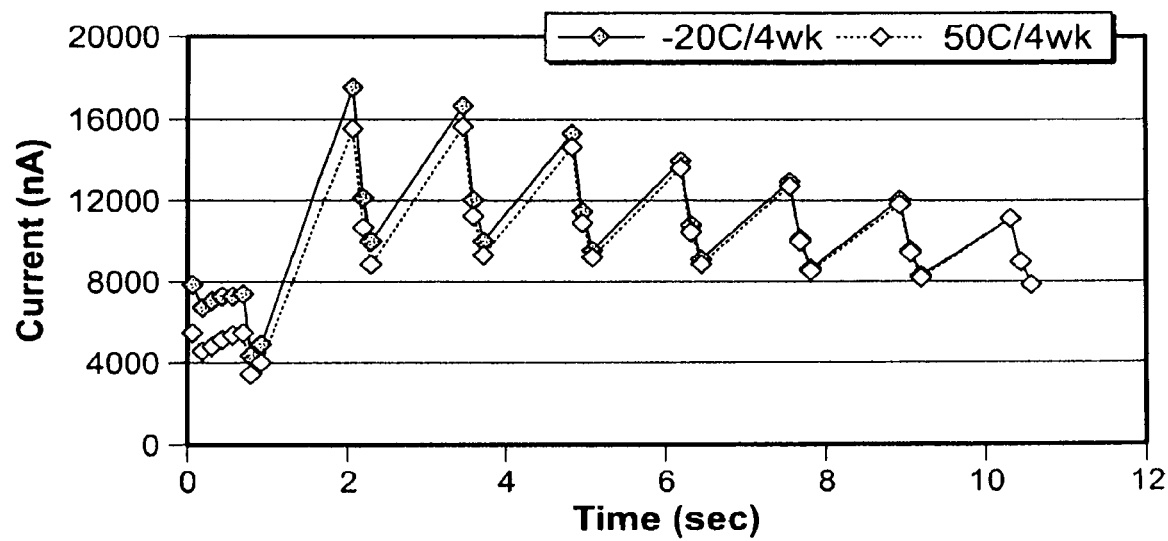
FIGS. 10a, 10b are plots of measured current values versus time in formulations having different inorganic salt concentrations.
Figure 10B:
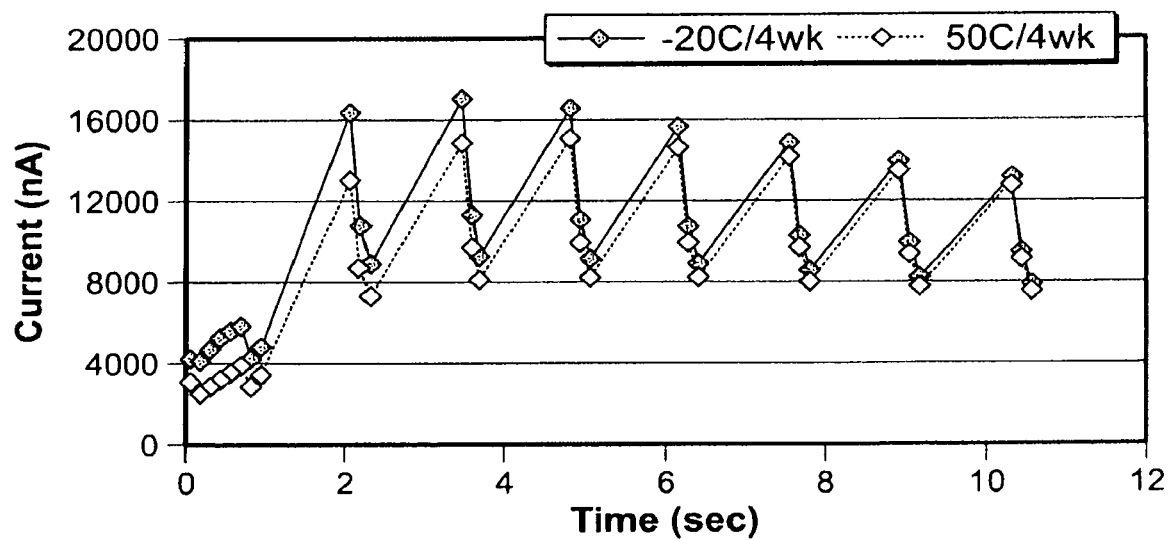

As shown in FIG. 10a, maximum kinetic performance was about 2 seconds for the samples that were stressed at −20° C. for 4 wks. The maximum kinetic performance was about 3.5 seconds for the samples that were stressed at −50° C. for 4 wks. Referring to FIG. 10b, the maximum kinetic performance was about 3.5 seconds for the samples that were stressed at −20° C. for 4 wks. and about 5 seconds for the samples that were stressed at −50° C. for 4 wks. Thus, formulations having a lower inorganic salt amount (e.g., FIG. 10a) had an improved maximum kinetic performance as compared to formulations with a higher inorganic salt amount (e.g., FIG. 10b).

In addition, lots of the formulation used in FIG. 10a with 2 second sensor-peak times were tested for assay bias or % bias. The % bias for glucose concentrations not greater than 100 mg/dL were less than about +/−2%. The % bias for a glucose concentration of 400 mg/dL was about +/−4%. The assay biases for lots of formulation used in FIG. 10b having 3-4 second sensor-peak times were also tested. The % bias for glucose concentrations not greater than 100 mg/dL were less than about +/−3%. The % bias for a glucose concentration of 400 mg/dL was about +/−10%. Thus, the assay biases for the lots having 3-4 second sensor-peak times were greater than the lots having 2 second sensor-peak times.

Example 9

Referring to FIG. 11, the coefficient of variation % (% CV) using 40% hematocrit whole blood samples at different glucose concentrations are shown. The glucose concentrations range from 36 mg/dL to 627 mg/dL. Reagent solutions having a low salt content lot were compared to reagent solutions having a high salt content lot. The low salt lot included 50 mM phosphate buffer at pH 6.5, 2 U/ul FAD-GDH, 40 mM 3-(2',5'-disulfophenylimino)-3H-phenothiazine having 5 wt. % sulfate, 0.25% hydroxyethyl cellulose-300 k and 0.2% MEGA 8 surfactant. The high salt lot included 100 mM phosphate buffer at pH 6.5, 2 U/ul FAD-GDH, 40 mM 3-(2',5'-disulfophenylimino)-3H-phenothiazine having 20 wt. % sulfate, 0.25% hydroxyethyl cellulose-300 k and 0.2% MEGA 8 surfactant.

The % CV was calculated by taking the mean of the maximum kinetic performance using sensor-peak times and dividing by the standard deviation of those sensor-peak times. This resulting value was multiplied by 100, resulting in the % CV. A total of 40 samples were tested for both the low salt reagent solutions and the high salt reagent solutions.

The low salt reagent solution reached maximum kinetic performance using sensor-peak times in less than 3 seconds, resulting in a better % CV for 40% hematocrit whole blood samples as compared to the higher salt reagent solution. The low salt reagent solutions had a much better % CV at the lower glucose concentration samples.

While the examples provided herein relate to in vitro applications of the test sensor reagents in accordance with the present invention, it is contemplated that these reagents may also be adapted for in vivo analyte monitoring by chemically immobilizing the mediators (e.g., by chemical reaction at one or more of the substituent groups on the aromatic rings), and incorporating the immobilized mediators into a device which can be implanted subcutaneously into a patient. The reagents of the embodiments described herein may also be used with continuous analyte monitoring systems.

Alternative Embodiment A

A reagent for detecting an analyte, the reagent comprising:
a flavoprotein enzyme;
a mediator selected from the group

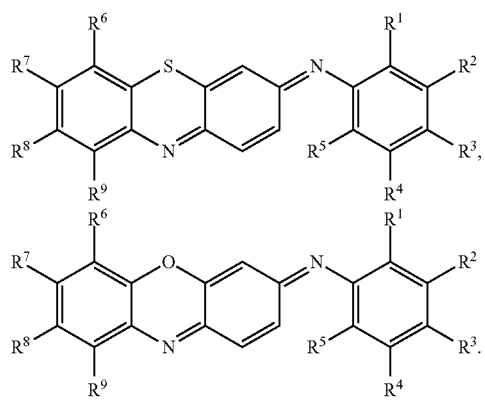

or a combination thereof, wherein $R^1$, $R^2$, $R^3$, $R^4$, $R^5$, $R^6$, $R^7$, $R^8$, and $R^9$ are the same or different, and are independently selected from the group consisting of hydrogen, alkyl, alkenyl, alkynyl, aryl, heteroaryl, cyclic, heterocyclic, halo, haloalkyl, carboxy, carboxyalkyl, alkoxycarbonyl, aryloxycarbonyl, aromatic keto, aliphatic keto, alkoxy, aryloxy, nitro, dialkylamino, aminoalkyl, sulfo, dihydroxyboron, and combinations thereof;
at least one surfactant;
a polymer; and
a buffer.

Alternative Embodiment B

The reagent of Alternative Embodiment A, wherein the flavoprotein enzyme is FAD-glucose dehydrogenase.

Alternative Embodiment C

The reagent of Alternative Embodiment A, wherein the mediator comprises 3-(2',5'-disulfophenylimino)-3H-phenothiazine.

Alternative Embodiment D

The reagent of Alternative Embodiment A, wherein the surfactant includes a saccharide-based surfactant or a phosphorylcholine-based surfactant.

Alternative Embodiment E

The reagent of Alternative Embodiment A, wherein the polymer is a cellulose-based polymer.

Alternative Embodiment F

The reagent of Alternative Embodiment A, wherein the buffer comprises a phosphate buffer.

Alternative Embodiment G

A reagent for detecting an analyte in a fluid sample, the reagent comprising: FAD-glucose dehydrogenase having an activity of from about 0.1 Units/µL to about 10 Units/µL;
a 3-(2',5'-disulfophenylimino)-3H-phenothiazine mediator having a concentration of from about 5 mM to about 120 mM;
a heptanoyl-N-methylglucamide surfactant having a concentration of from about 0.05 wt. % to about 0.5 wt. % of the reagent; and
a hydroxyethyl cellulose polymer having a concentration of from about 0.1 wt. % to about 4 wt. % of the reagent.

Alternative Embodiment H

The reagent of Alternative Embodiment G further comprising a phosphate buffer.

Alternative Embodiment I

The reagent of Alternative Embodiment H, wherein the phosphate buffer has a concentration of from about 25 mM to about 200 mM and a pH of from about 4 to about 8.

Alternative Embodiment J

The reagent of Alternative Embodiment I, wherein the phosphate buffer has a concentration of from about 50 mM to about 150 mM and a pH of from about 6 to about 7.

Alternative Embodiment K

The reagent of Alternative Embodiment G, wherein the reagent comprises FAD-glucose dehydrogenase having an activity of from about 0.5 Units/μL to about 2.5 Units/μL, a 3-(2',5'-disulfophenylimino)-3H-phenothiazine mediator having a concentration of from about 30 mM to about 60 mM, a heptanoyl-N-methylglucamide surfactant having a concentration of from about 0.1 wt. % to about 0.4 wt. % of the reagent, and a hydroxyethyl cellulose polymer having a concentration of from about 0.2 wt. % to about 0.5 wt. % of the reagent.

Alternative Embodiment L

An electrochemical test sensor comprising:
a working electrode having a surface;
a counter electrode having a surface; and
a reagent coating at least a portion of the surface of the working electrode and at least a portion of the surface of the counter electrode, the reagent comprising a flavoprotein, a phenothiazine or a phenoxazine mediator, a buffer, and at least one surfactant and a polymer.

Alternative Embodiment M

The sensor of Alternative Embodiment L, wherein the flavoprotein includes FAD-glucose dehydrogenase.

Alternative Embodiment N

The sensor of Alternative Embodiment L, wherein the phenothiazine mediator includes 3-(2',5'-disulfophenylimino)-3H-phenothiazine.

Alternative Embodiment O

The sensor of Alternative Embodiment L, wherein the at least one surfactant includes a heptanoyl-N-methylglucamide.

Alternative Embodiment P

The sensor of Alternative Embodiment L, wherein the polymer is a cellulose-based polymer.

Alternative Process Q

A method of detecting an analyte in a fluid sample, the analyte undergoing a chemical reaction, the method comprising the acts of:
providing an electrode surface;
facilitating flow of the fluid sample to the electrode surface using at least one surfactant;
catalyzing the chemical reaction with a flavoprotein enzyme;
generating a redox equivalent by the chemical reaction; and
transferring the redox equivalent to the electrode surface using a phenothiazine or a phenoxazine mediator.

Alternative Process R

The method of Alternative Process Q, wherein the electrode surface includes a working electrode and a counter electrode, the electrode surface including a reagent comprising the at least one surfactant, the flavoprotein enzyme, the phenothiazine mediator, and a buffer.

Alternate Process S

The method of Alternative Process R, wherein the reagent further includes a cellulose-based polymer.

Alternate Process T

The method of Alternative Process S, wherein the polymer is a cellulose-based polymer.

Alternate Process U

The method of Alternative Process R, wherein the buffer includes a phosphate buffer.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents, and alternatives falling within the spirit and scope of the invention.

What is claimed is:

1. An electrochemical test sensor comprising:
a working electrode having a surface;
a counter electrode having a surface; and
a reagent coating at least a portion of the surface of the working electrode and at least a portion of the surface of the counter electrode, the reagent comprising FAD-glucose dehydrogenase, a 3-(2',5'-disulfophenylimino)-3H-phenothiazine mediator having about 5 wt. % sulfate, a phosphate buffer, a surfactant, and a hydroxyethyl cellulose polymer, wherein at least one of the mediator and the buffer includes an inorganic salt, and a ratio of the total inorganic salt to mediator is less than about 3:1.

2. The sensor of claim 1, wherein the ratio of the total inorganic salt to mediator is in a ratio of less than about 2:1.

3. The test sensor of claim 1, wherein the reagent includes about 2.00 U/μL of the FAD-glucose dehydrogenase enzyme, about 40 mM of the 3-(2',5'-disulfophenylimino)-3H-phenothiazine enzyme, about 50 mM of the buffer, about 0.20 wt. % of heptanoyl-N-methylglucamide surfactant, and about 0.25 wt. % of the hydroxyethyl cellulose polymer.

4. The test sensor of claim 1, wherein the buffer is a phosphate buffer, the reagent including about 30 mM of the phosphate buffer.

5. The test sensor of claim 1, wherein the FAD-glucose dehydrogenase has an activity of from about 0.5 Units/μL to about 2.5 Units/μL, the 3-(2',5'-disulfophenylimino)-3H-phenothiazine mediator has a concentration of from about 30 mM to about 60 mM, the surfactant being a heptanoyl-N-methylglucamide surfactant having a concentration of from about 0.1 wt. % to about 0.4 wt. % of the reagent, and the hydroxyethyl cellulose polymer has a concentration of from about 0.2 wt. % to about 0.5 wt. % of the reagent.

6. The test sensor of claim 1, wherein the FAD-glucose dehydrogenase has an activity of about 1.75 Units/μL, the 3-(2',5'-disulfophenylimino)-3H-phenothiazine mediator has a concentration of about 40 mM, the surfactant having a concentration of about 0.2 wt. %, the hydroxyethyl cellulose has a concentration of about 0.25 wt. %, and the buffer being a phosphate buffer having a concentration of about 100 mM.

7. The test sensor of claim 6, wherein the coefficient of variation of the reagent is between about 1.2 and about 3.4.

8. The test sensor of claim 1, wherein the buffer is a phosphate buffer, the reagent including about 50 mM of the phosphate buffer at a pH of about 6.5, about 0.25% of the hydroxyethyl cellulose polymer, about 0.2% of heptanoyl-N-methylglucamide surfactant, and about 40 mM of the 3-(2',5'-disulfophenylimino)-3H-phenothiazine mediator, wherein the FAD-glucose dehydrogenase has an activity of about 2 Units/μL, and wherein the coefficient of variation of the reagent is between about 1.4 and about 2.7.

* * * * *